US011213291B2

(12) United States Patent
Jacquemin

(10) Patent No.: US 11,213,291 B2
(45) Date of Patent: Jan. 4, 2022

(54) DURAL REPAIR DEVICE

(71) Applicant: John Jacquemin, Cincinnati, OH (US)

(72) Inventor: John Jacquemin, Cincinnati, OH (US)

( * ) Notice: Subject to any disclaimer, the term of this patent is extended or adjusted under 35 U.S.C. 154(b) by 0 days.

(21) Appl. No.: 16/758,246

(22) PCT Filed: Oct. 25, 2018

(86) PCT No.: PCT/US2018/057430
§ 371 (c)(1),
(2) Date: Apr. 22, 2020

(87) PCT Pub. No.: WO2019/084220
PCT Pub. Date: May 2, 2019

(65) Prior Publication Data
US 2020/0246000 A1  Aug. 6, 2020

Related U.S. Application Data

(60) Provisional application No. 62/577,392, filed on Oct. 26, 2017.

(51) Int. Cl.
*A61B 17/062* (2006.01)
*A61B 17/00* (2006.01)
*A61B 17/04* (2006.01)

(52) U.S. Cl.
CPC .. *A61B 17/062* (2013.01); *A61B 2017/00477* (2013.01); *A61B 2017/00867* (2013.01);
(Continued)

(58) Field of Classification Search
CPC ........ A61B 17/062; A61B 2017/00477; A61B 2017/00867; A61B 2017/00876;
(Continued)

(56) References Cited

U.S. PATENT DOCUMENTS 3,842,840 A   10/1974   Schweizer
5,053,046 A   10/1991   Janese
(Continued)

FOREIGN PATENT DOCUMENTS

WO     96/39948 A1     12/1996
WO     2015/109159 A1   7/2015

OTHER PUBLICATIONS

Supplemental Search Report for search completed Jun. 9, 2021 from corresponding European Application No. 18871005.7 dated Jun. 18, 2021.
(Continued)

*Primary Examiner* — George J Ulsh
(74) *Attorney, Agent, or Firm* — Porter Wright Morris & Arthur LLP

(57) ABSTRACT

A dural repair device operable with a single hand. The device comprises a handle and an outer arm having an end opening and a mechanism for holding a needle within the outer arm. The device also comprises an inner arm including a heel, a platform, an end opening, and a mechanism for catching a needle. The handle is activatable such that the inner and outer arms couple, the needle is caught by the mechanism for catching a needle within the inner arm, and when the inner and outer arms are uncoupled, the needle is transferred from the outer arm to the inner arm.

20 Claims, 8 Drawing Sheets

(52) U.S. Cl.
CPC .............. *A61B 2017/00876* (2013.01); *A61B 2017/0474* (2013.01)

(58) Field of Classification Search
CPC . A61B 2017/0474; A61B 17/04; A61B 17/28; A61B 17/0469; A61B 17/0487; A61B 17/0625; A61B 2017/0454; A61B 2017/0458; A61B 17/0485; A61B 2017/0488; A61B 2017/2926
See application file for complete search history.

(56) References Cited

U.S. PATENT DOCUMENTS

| | | | |
|---|---|---|---|
| 5,562,699 A | 10/1996 | Heimberger et al. | |
| 5,730,747 A * | 3/1998 | Ek | A61B 17/0469 606/139 |
| 6,322,570 B1 | 11/2001 | Matsutani et al. | |
| 8,246,638 B2 | 8/2012 | Perez-Cruet et al. | |
| 8,690,898 B2 * | 4/2014 | Hatch | A61B 17/06066 606/144 |
| 8,795,296 B2 | 8/2014 | Perez-Cruet et al. | |
| 8,821,518 B2 | 9/2014 | Saliman et al. | |
| 10,052,098 B2 * | 8/2018 | Hatch | A61B 17/0469 |
| 2006/0276840 A1 | 12/2006 | Perper et al. | |
| 2010/0130990 A1 | 5/2010 | Saliman | |
| 2013/0046335 A1 | 2/2013 | Deutsch et al. | |
| 2014/0236194 A1 | 8/2014 | Deutsch et al. | |
| 2015/0142018 A1 | 5/2015 | Sniffin et al. | |
| 2016/0174966 A1 | 6/2016 | Djurovic | |

OTHER PUBLICATIONS https://www.medline.com/product/Castroviejo-Needle-Holder-Forceps/Needle-Holder-Forceps/Z05-PF14525, downloaded Jun. 2017.
http://www.scanlaninternational.com/products/3003-342, downloaded Jun. 2017.
Covidien Endo Stitch Manual, 2008.

* cited by examiner

DURAL REPAIR DEVICE

TECHNICAL FIELD

The present invention relates to devices and methods for dural repair. More specifically, the invention relates to dural repair devices operable with a single hand wherein activation of a handle can move arms of the device to transfer a needle during suturing of a dural tear so as to allow repair without damaging nerves.

BACKGROUND

Spinal surgery in the United States is increasing in volume and complexity. Movements and trends to allow surgery with decreased morbidity and faster healing time are becoming more popular and are collectively known as minimally invasive procedures.

Spinal surgery often involves working around the spinal cord and nerves which are contained in spinal fluid. The fluid is held in place by tissue called the dura, which creates the thecal sac allowing the tissues to "float" within it. The dura can be torn as the result of injury.

Repair of these injuries is commonly done with a direct repair of this tissue by sewing the two sides of the torn dura back together. However these procedures are limited by the fact the nerves within the sac push up through the tear, complicating closure and increasing the likelihood of nerve damage. Additionally, the tear can be located in a position where passage of a needle is difficult, or where the suture line or circumference of a repair or knot strangulates one or more nerves.

Current devices, suture types, and needles are often too large for working within the limited spaces required for minimally invasive procedures. This results in repair including a step of increasing the size of the exposed area of tissue to allow for adequate closure. This defeats the purpose of a minimally invasive procedure.

There is a continuing need for improved devices and methods allowing for closure of a dural tear while protecting nerves and the spinal cord from being included in a suture and knot or otherwise damaged during closure. Such devices and methods are described herein.

SUMMARY

The invention is generally directed to a dural repair device operable with a single hand, the device comprising: a handle; an outer arm comprising an end opening and a mechanism for holding a needle therewithin; an inner arm comprising a heel, a platform, an end opening, and a mechanism for catching the needle; and wherein the handle is activatable such that the inner and outer arms couple, the needle is caught by the mechanism for catching the needle within the inner arm, and when the inner and outer arms are uncoupled, the needle is transferred from the outer arm to the inner arm.

Additional embodiments are directed to a dural repair device operable with a single hand, the device comprising: a top section comprising a handle comprising opposable arms squeezable by a single hand such that the opposable arms move toward one another and each of the opposable arms move toward a longitudinal midline of the device; a bottom section comprising opposable, coupleable arms, wherein the arms comprise an outer arm and an inner arm that oppose one another and which move toward the longitudinal midline of the device upon squeezing of the handle; wherein: the outer arm comprises: a bottom surface; an end opening; and a mechanism for holding a needle therewithin; the inner arm comprises: a heel; a platform that is from about 2 mm to about 4 mm in length that is slidable under an edge of dura so as to push rootlets away from the needle; an end opening; and a mechanism for catching the needle therewithin; and when the handle is squeezed such that the bottom section arms couple, the needle held within the outer arm is caught within the inner arm such that when the handle is released, the needle moves from the outer arm to the inner arm, and throughout repair of the dura by suturing via the device, the needle is protected from catching the rootlets.

Specific embodiments are directed to a method for dural repair, the method comprising: providing a device comprising: a handle; an outer arm comprising an end opening and a mechanism for holding a needle therewithin; an inner arm comprising a heel, a platform, an end opening, and a mechanism for catching the needle; positioning the outer arm and the inner arm of the device such that each of the arms straddles a side of a torn dura; pushing at least a portion of a nerve, rootlet, or spinal cord away from the device with a portion of the inner arm to prevent the nerve, rootlet, or spinal cord from being included in a suture line or knot; squeezing the handle of the device such that the inner and outer arms couple, and the needle is caught by the mechanism for catching the needle within the inner arm; releasing the handle such that the inner and outer arms uncouple, and the needle is transferred from the outer arm to the inner arm; withdrawing the device from the dura, pulling suture coupled to the needle through the dura.

Additional aspects and advantages of the invention will be apparent in view of the description below.

BRIEF DESCRIPTION OF THE DRAWINGS

The embodiments set forth in the drawings are illustrative and exemplary in nature and not intended to limit the invention defined by the claims. The following detailed description of the illustrative embodiments can be understood when read in conjunction with the following drawings, in which:

DETAILED DESCRIPTION

Figure 1:
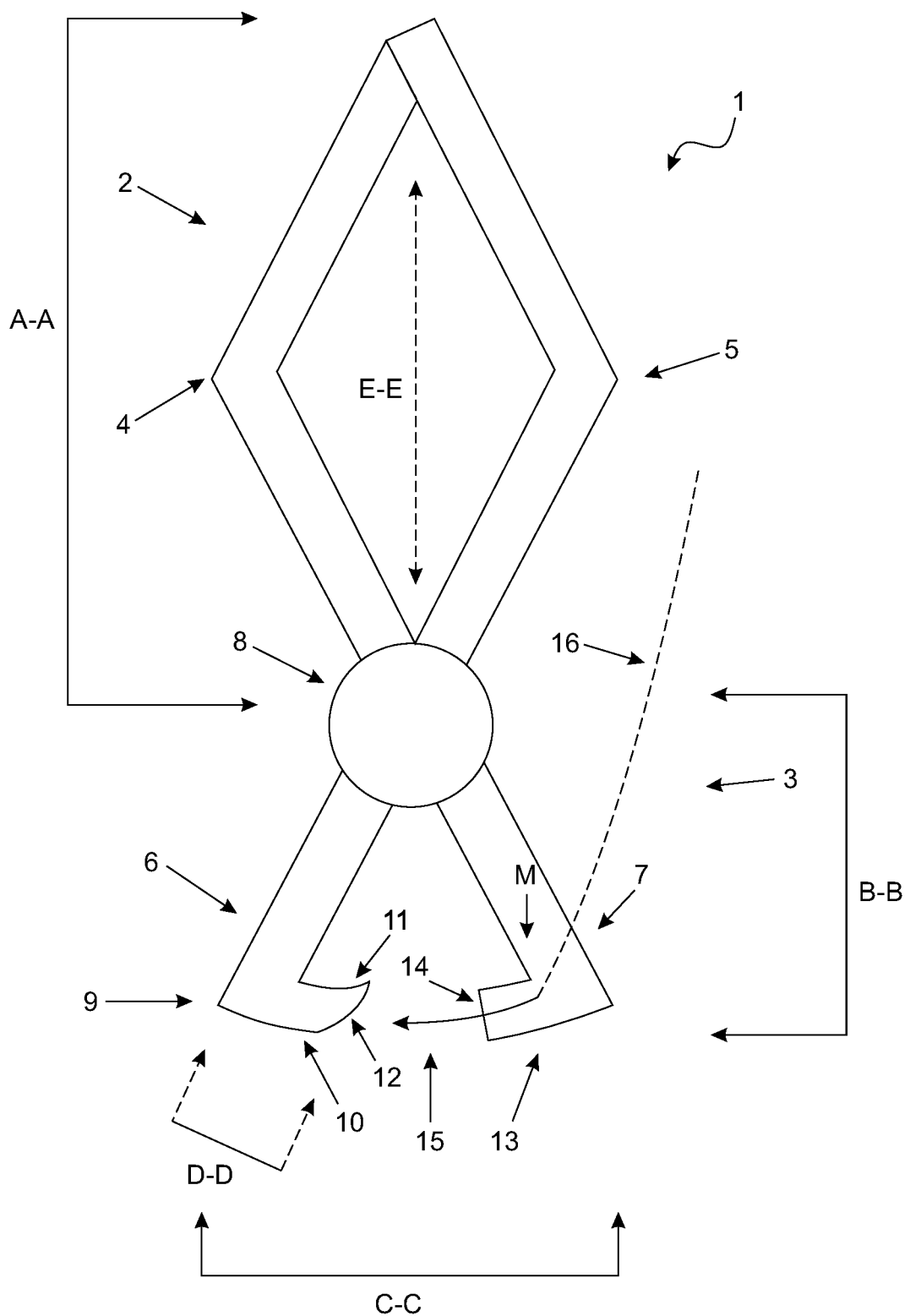
FIG. 1 illustrates an embodiment of a dural repair device as detailed herein.

Specific embodiments of the present disclosure will now be described. The invention can, however, be embodied in different forms and should not be construed as limited to the embodiments set forth herein. Rather, these embodiments are provided to illustrate more specific features of certain aspects of the invention to those skilled in the art.

Unless otherwise defined, all technical and scientific terms used herein have the same meaning as commonly understood by one of ordinary skill in the art to which embodiments of this invention belong. The terminology used herein is for describing particular embodiments only and is not intended to be limiting of the invention. As used in the specification and appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about," which is intended to mean up to ±10% of an indicated value. Additionally, the disclosure of any ranges in the specification and claims are to be understood as including the range itself and also anything subsumed therein, as well as endpoints. Numerical ranges as used herein are intended to include every number and subset of numbers within that range, whether specifically disclosed or not. Unless otherwise indicated, the numerical properties set forth in the specification and claims are approximations that can vary depending on the desired properties sought to be obtained in embodiments of the present invention. Notwithstanding that numerical ranges and parameters setting forth the broad scope of embodiments of the invention are approximations, the numerical values set forth in the specific examples are reported as precisely as possible. Any numerical values, however, inherently contain certain errors necessarily resulting from error found in their respective measurements.

The dura and surrounding tissue structures are known in the art. Such structures are detailed in the text *The Human Brain and Spinal Cord: Functional Neuroanatomy and Dissection Guide* by Lennart Heimer, which is herein incorporated by reference in its entirety. Such structures are detailed in *Clinical Anatomy of the Spine, Spinal Cord, and ANS*, by Gregory D. Cramer DC ad Susan A. Darby PhD, which is also herein incorporated by reference in its entirety.

The term "platform" as used herein, unless otherwise specified, refers to a portion of the inner arm useable for putting pressure on a portion of a nerve, rootlet, or spinal cord. In specific embodiments the pressure is aimed to result in movement of a part of a nerve, rootlet, and/or spinal cord. In specific embodiments the platform is also useable for putting pressure on tissue surrounding the nerve, rootlet, or spinal cord. In specific embodiments the platform is also useable for putting pressure on the nerve, rootlet, and/or spinal cord and/or putting pressure on tissue surrounding the nerve, rootlet, or spinal cord without causing damage to the material pressed.

The term "heel" as used herein, unless otherwise specified, refers to the place at which the platform meets the portion of the inner arm running essentially longitudinally back toward the coupling at the central region of the device. In specific embodiments the heel includes a sharp or otherwise angled region as one moves from the platform to the essentially longitudinally running section of the inner arm. In specific embodiments the heel and platform form a continuous curve.

The term "handle" as used herein, unless otherwise specified, refers to a section of the device that can be used to move the inner and/or outer arm. In specific, non-limiting embodiments, the device has a top section comprising two opposing upper arms that together act as an embodiment of the handle. Various additional handle embodiments are described herein.

The term "activate" as used herein in reference to the handle, unless otherwise specified, refers to mechanically or electronically causing movement of at least a portion of the handle, directly or indirectly, so as to move the inner and/or outer arm.

FIG. 1 illustrates a dural repair device 1. The device has a top section 2 with an example length A-A, a bottom section 3 with an example length B-B, and the bottom section 3 has an example width C-C when the dural repair device is in an open position. The top section 2 comprises two opposing upper arms, 4 and 5, that together can act as an embodiment of the handle and which is squeezable by a single hand such that arms 4 and 5 move toward one another and each moves toward a longitudinal midline E-E of the device 1. The bottom section 3 comprises two opposing arms, an inner arm 6 and an outer arm 7. The device 1 can have a coupling 8 positioned substantially between the top section 2 and bottom section 3. The inner arm 6 has a heel 9, a platform 10 with an example length D-D, a tip 11, and an end opening 12. In specific embodiments the platform 10 can be formed of a straight line. In specific embodiments, the angle between the platform 10 and the inner arm 6 is about 45 degrees, or from about 25 degrees to about 65 degrees, or from about 30 degrees to about 60 degrees, or from about 40 degrees to about 50 degrees. The outer arm 7 has a bottom surface 13 and an end opening 14. In specific embodiments the outer arm 7 comprises a mechanism M for holding a needle 15 therewithin and the needle 15 can be coupled to suture 16. Specific embodiments of the mechanism M can include a direct attachment to an inner wall of the outer arm 7 or attachment to an extension coupled to the inner wall of the inner arm. For example, the attachment could include adhesives, or attachment via a breakable clip, or the needle 15 could be hooked via a loop or other attachment to a protrusion or protrusions extending up from the inner wall of the outer arm 7. The protrusion or protrusions can be at any angle or a series of angles from the inner wall of the outer arm 7, such as from about 0 to about 90 degrees. The protrusions can extend from the inner top, inner bottom, or inner side of the outer arm, or in between. FIG. 1 provides non-limiting examples of mechanism M, and various other mechanisms M are described and illustrated herein.

In specific embodiments the inner arm 6 comprises the tip 11 extending out toward the longitudinal midline E-E of the device 1 farther than any portion of the platform 10 or heel 9. In specific embodiments the tip 11, platform 10, or heel 11 have at least one curved portion that is slidable under an edge of dura and is/are configured to push rootlets away from the device 1. In specific embodiments the platform 10 comprises a continuous curve.

In specific embodiments, the length of the platform 10 is less than 6 mm, or less than about 5 mm, or less than about 4 mm, or less than about 3 mm. In specific embodiments, the length of the platform 10 is from about 1 mm to about 5 mm, or from about 2 mm to about 4 mm, or from about 2.5 mm to about 3.5 mm.

In specific embodiments, a maximum distance between the outer arm 7 and inner arm 6 end openings (14, 12) is less than about 2 cm, or less than about 1 cm, or less than about 0.5 cm. In specific embodiments the maximum distance between the outer arm 7 and inner arm 6 end openings (14, 12) is from about 0.25 cm to about 2 cm, or from about 0.5 cm to about 1 cm.

Figure 2:
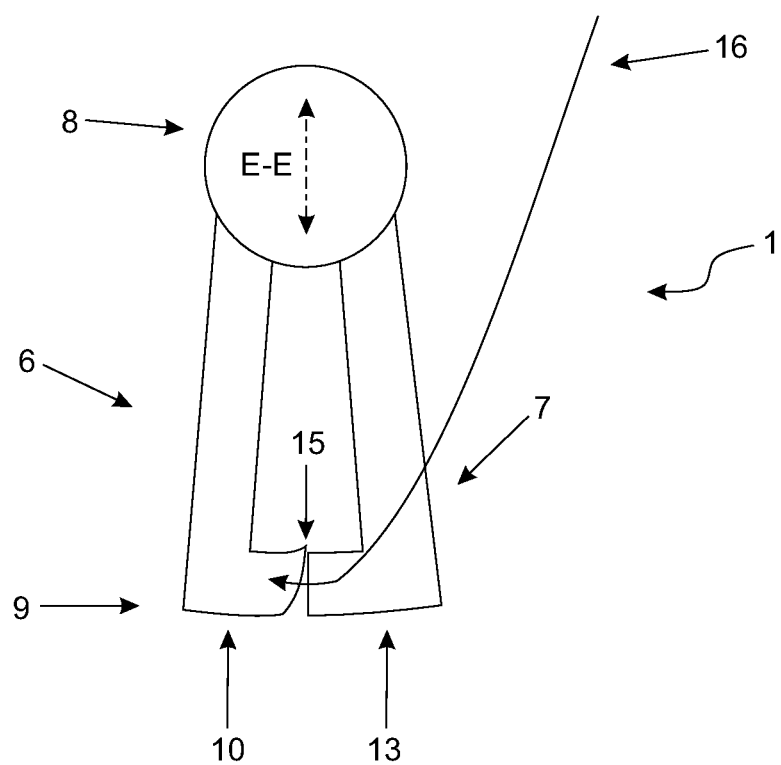
FIG. 2 illustrates the dural repair device of FIG. 1 in a closed position.

FIG. 2 illustrates the dural repair device 1 of FIG. 1 in a closed position. When the two opposing upper arms 4 and 5 (not shown in FIG. 2) are moved toward one another, the two opposing arms, inner arm 6 and outer arm 7 respectively, move toward one another, and toward the longitudinal midline E-E of the device. The opposing upper arms 4 and 5 can be moved toward each other such that inner arm 6 and outer arm 7 are moved so as to couple. The needle 15 can be contained within the outer arm 7. FIG. 2, for completeness, also depicts the coupling 8, heel 9 and platform 10 of the inner arm 6, the bottom surface 13 of the outer arm 7, the needle 15, and the suture 16.

Figure 3:
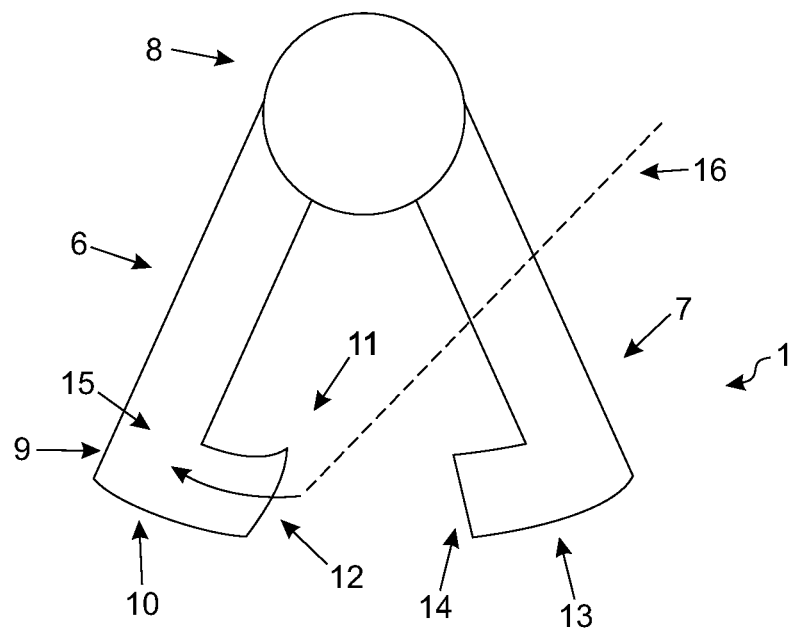
FIG. 3 illustrates the dural repair device of FIG. 1 upon needle passage from the outer arm to the inner arm of the device.

FIG. 3 illustrates the dural repair device 1 where the upper arms 4 and 5 (not shown in FIG. 3) were moved toward one another such that inner arm 6 and the outer arm 7 coupled, and the needle 15 was passed from outer arm 7 inner arm 6. In specific embodiments upon handle activation the needle 15 transfers, and more specifically, the needle 15 is initially in specific embodiments held completely within the outer arm 7, and after the transfer of the needle 15 to the inner arm 6 the needle 15 is held completely within the inner arm 6, and no portion of the needle 15 passes either of the arm (7, 6) openings (14, 12) until after the arms (7, 6) couple. In specific embodiments the inner arm 6 comprises a mechanism (not shown in FIG. 3) for catching the needle 15. This mechanism can be a depression within a wall of the inner arm 6. The depression can be a groove or series of grooves. The mechanism can include a depression matching at least part of the shape of the needle 15. The mechanism can as also be a hole or holes through the inner arm 6. The mechanism can also be a catch or series of catches extending up from the inner wall of the inner arm and the same or mixed angles. An extending catch can be at an angle such as from about 0 to about 90 degrees in relation to the inner surface of the inner arm 6 (such as from about 25 to about 75, and/or from about 40 to about 60, and/or from about 75 to about 90 degrees). An extending catch can also have a loop or adhesive for catching the needle 15. The extending catch can be formed of a ring extending out from the inner arm 6, or can be formed of a magnet. FIG. 3, for completeness, also depicts the coupling 8, heel 9, platform 10, and tip 11 of the inner arm 6, the bottom surface 13 of the outer arm 7, and the suture 16.

In specific embodiments the outer arm 7 and the inner arm 6 are formed of a single piece. In other embodiments, the arms (7, 6) are formed separately. In either case the coupling 8 can be used to draw together a single piece of metal used to form both arms (7, 6) and/or can be used to form a substantially figure-eight formation where the metal overlaps itself (7, 6). The handle can comprise a shape-memory alloy such as nickel-titanium (NiTi). The coupling 8 can include slots for the arms (7, 6) and/or handle portions to slide through. The coupling 8 can include a ratchet mechanism therewithin or coupled thereto, such that squeezing of the handle leads to locking in of arms (7, 6) at multiple opening positions; in such a case a mechanism for ratchet release can include a side-button on the device 1, or a simple pressure mechanism such that upon reaching the closed position where the arms (7, 6) couple, a further forcing together of the upper arms 4 and 5 by squeezing the handle releases the ratchet to the open position.

EXAMPLES

Figure 4:
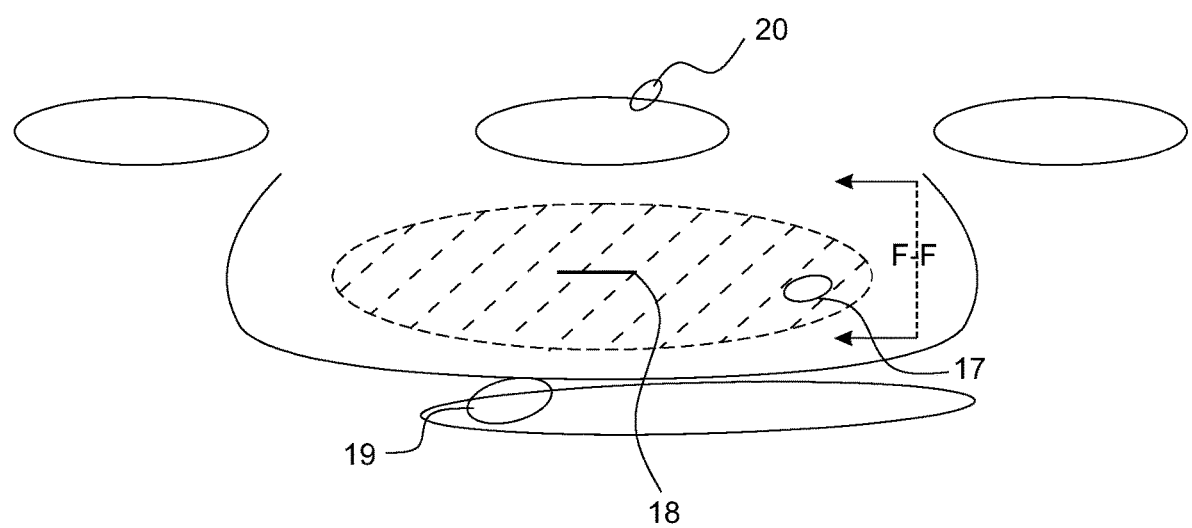
FIG. 4 illustrates a region for repair of the dura.

Embodiments of the device outlined herein show surprising effectiveness in results for methods of repairing injuries to the dura. Current technologies tend to lead to additional injuries or require cerebrospinal fluid drainage for localized repair. Methods described herein can be used when the dura has been damaged due to direct injury by instruments and/or during removal of attached tissues including scar tissue, a cyst, a disc, and/or ligamentum flavum. FIG. 4 illustrates a region for repair of the dura. Shown is the dura 17 and a tear 18 of the dura 17. Also shown for context is a facet joint 19, and spinous process 20. As indicated, an example distance is shown as F-F. In specific embodiments F-F is less than 1 cm in length.

Example 1: Device Loading. In specific embodiments the entire device 1 is preloaded with 6-OProlene® type suture 16 and needle 15. The needle 15 and platform 10 meet when the handle is squeezed or the needle 15 may be free and then moved by separate forcep or caught by the catch of the inner arm 6. At least a portion of the inner arm 7 slides under the edge of the dura 17 pushing rootlets 21 and has a groove that matches the needle 15 and catches or accepts it. The handle is squeezed and two upper arms, 4 and 5, come together. The needle 15 is protected and rootlets 21 can't be caught in a portion of the needle 15 and/or suture 16 during repair.

Sutures for methods and devices as described herein can include one or a combination or combinations of monofilament, multifilament synthetic, biological, absorbable, and/or non-bioabsorbable sutures. Non-limiting examples of monofilament sutures include Monocryl®, Ethilon®, Prolene®, and/or PDS® II polydioxanone. Non-limiting examples of multifilament sutures include Vicryl®, Silk sutureVicryl Plus®, Vicryl Rapide®, Silk suture such as PERMA-HAND® Silk Suture, Ethibond®, and/or Mersilene®. Non-limiting examples of synthetic sutures include Monocryl®, Mersilene®, Ethilon®, Vicryl®, Vicryl Plus®, Vicryl Rapide®, Ethibond®, Prolene®, and/or PDS® II. A non-limiting example of a biological is silk suture. Non-limiting examples of absorbable sutures include Monocryl®, Vicryl®, Vicryl Plus®, Vicryl Rapide®, and/or PDS II. Non-limiting examples of non-absorbable sutures include Mersilene®, Ethilon®, Silk Suture®, Ethibond®, and/or Prolene. Non-limiting examples of suture material can include one or more of: stainless steel, polyester, polypropylene, nylon, and/or cotton. Needles use herein can be curved or straight.

The device 1 handle or other portions can be made partially or entirely out or a metal or metals or a composite of materials. In a specific example, part or all of the device comprises a shape-memory material. In a specific example, part or all of the device comprises one or more of copper-aluminium-nickel, nickel-titanium (NiTi), zinc, copper, gold and/or iron.

Example 2: Dura is partially torn, but there is no leak of cerebrospinal fluid from the spinal canal. Rootlets float and are next to site of the repair. If the fluid is drained then they would sink and repair would be easier but rather than complete the tear to then fix the tear, the methods provided herein can be used to fix the original, partial tear. The methods provided herein can fix the tear wherein cerebrospinal fluid is not drained during the repair procedure. At least a portion of the inner arm 6, such as the platform 10, can be used to safely push a nerve, rootlet, or portion of the spinal cord away from the device such that a suture 15 or needle 16 does not touch or otherwise damage the nerve, rootlet, or portion of the spinal cord, even when any of these are floating in cerebrospinal fluid.

Figure 5:
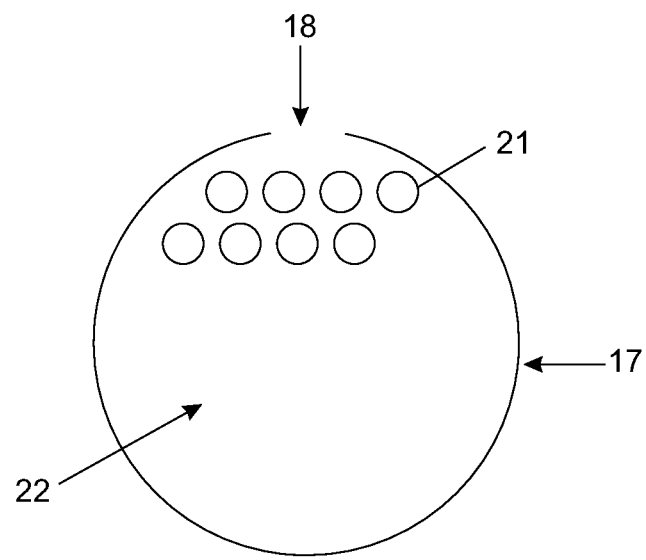
FIG. 5 illustrates a partially torn dura, with no leak of cerebrospinal fluid from the spinal canal.
Figure 6:
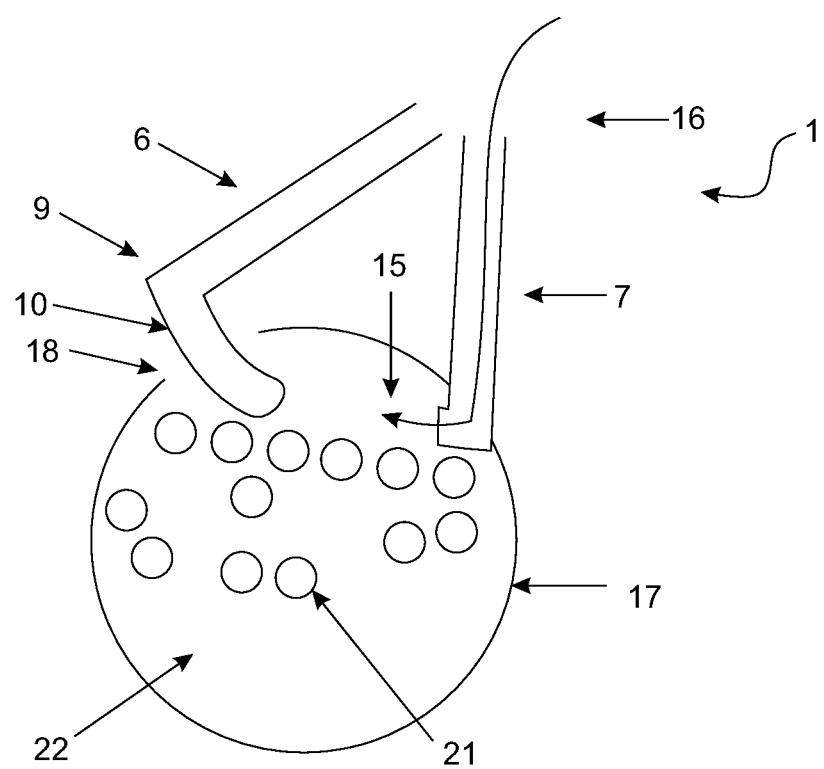
FIG. 6 illustrates repair of a partially torn dura.

This is illustrated in FIG. 5, which illustrates the dura 17, tear 18, rootlets 21, and space containing cerebrospinal fluid 22. FIG. 6 illustrates placement of the device 1 such that the inner arm 6 and outer arm 7 are on opposite sides of the dura 17, and there is a dural tear 18 with no leak of cerebrospinal fluid. In FIG. 6 the platform 10 is used to move floating rootlets 21 away from the device 1 so as to protect the rootlets 21 from the needle 15. FIG. 6 also illustrates the space containing cerebrospinal fluid 22 and the heel 9 of the inner arm 6. Though in FIG. 6 the needle 15 is shown as partially exposed from the end opening 14 of the outer arm 7, various embodiments contemplate the needle 15 being held fully within the outer arm 7, partially within the outer arm 7, and/or beyond the outer arm 7 end opening 14. More specifically, the needle 15 can be held within the outer arm 7 so as to prevent any interaction with rootlets 21; alternatively, the needle 15 can be held so that it is partially exposed, with the needle 15 held such that a portion is within the outer arm 7 and a portion is exposed toward the space containing cerebrospinal fluid 22. Alternatively, an embodiment could include exterior placement of the needle 15 in relation to the outer arm 7 end opening 14. The needle 15 can be, in specific embodiments, held by jaws either within, partially within, or outside of the outer arm 7.

Figure 7:
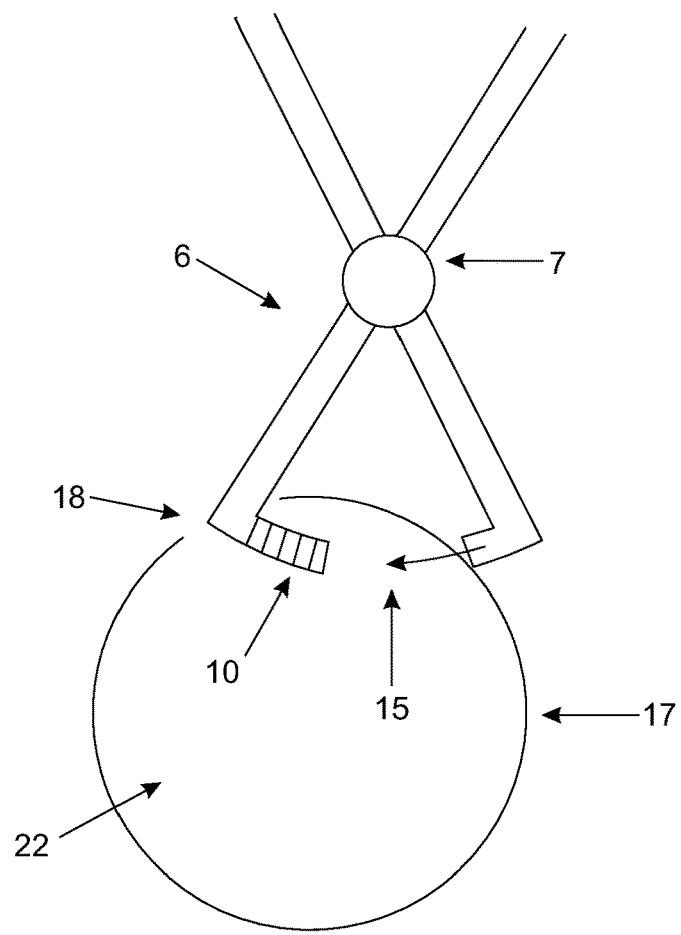
FIG. 7 illustrates a continuation of the repair of the tear of FIG. 6 where the rootlets have been successfully pushed by the platform from the area within the space containing cerebrospinal fluid.
Figure 8:
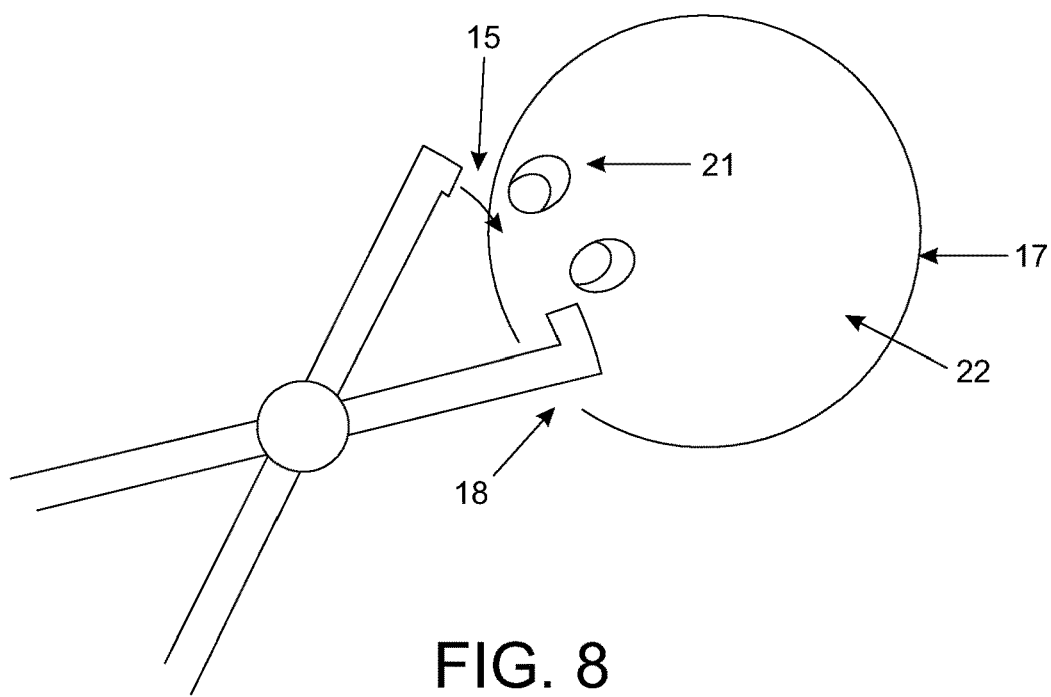
FIG. 8 illustrates a continuation of the repair of the tear of FIG. 7, where the device arms are separated as the handle is released and suturing through the dura can be performed.

FIG. 7 shows a continuation of the repair of the tear 18 of the dura 17 of FIG. 6, where the rootlets 21 (not shown in FIG. 7) have been successfully pushed by the platform 10 from the area within the space containing cerebrospinal fluid 22, and needle 15 can be passed from the outer arm 7 to the inner arm. As shown in FIG. 7, the platform 10 can be multisegmented so as to allow a platform shape with one or more than one curves, or a specific shape as required for a given surgery. FIG. 8 illustrates continued repair of the tear 18 of the dura 17. Once the needle 15 is caught by the inner arm 6, the inner 6 and outer 7 arms are separated as the handle is released, the thread can be pulled through the dura 17. As this occurs, the rootlets 21 can float in the space containing cerebrospinal fluid 22 back toward the dura 17 and the site of repair, without being damaged. The process of suturing can then be repeated until complete closure of the dura 17 is achieved. The outer arm 7 is configured such that a needle 15 can be manually loaded, or it can be set to be preloaded with multiple needles 15 and can be configured so that one needle 15 is released from within the outer arm 7 so as to be held for use once a needle 15 has been used. The inner arm 6 can be configured for manual or electronic removal of the needle 15 from the catch. In specific embodiments one needle 15 is reused and manually or mechanically moved back to the outer arm 7 for reuse.

Figure 9:
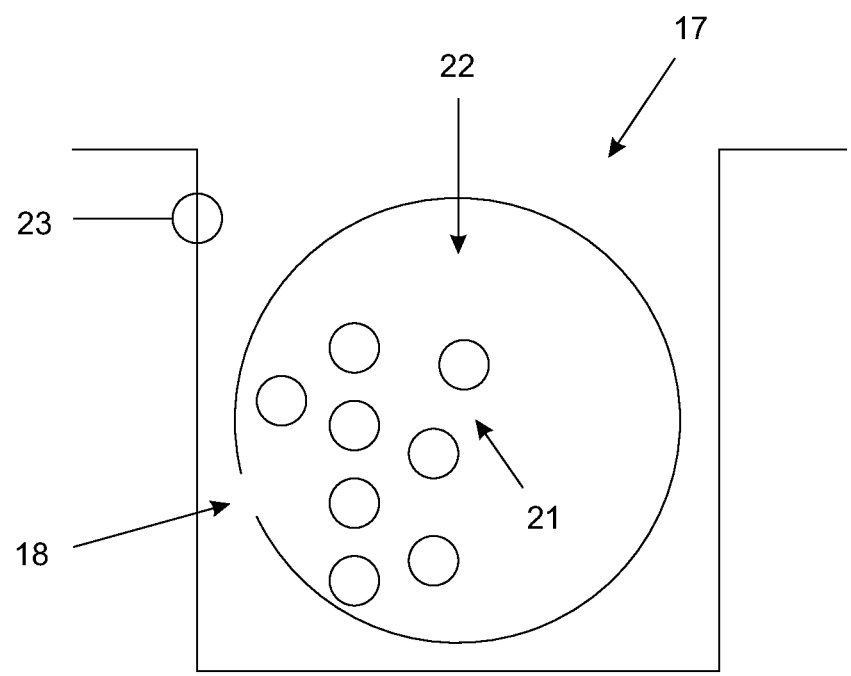
FIG. 9 illustrates repair of a torn dura located at a bony side wall of the spinal canal.

Example 3: Repairing dural tears at the edge of dissection when the needle is too big to make a throw without catching rootlets. Methods described herein can be used when torn dura comprises a tear located at a bony side wall of the spinal canal. This is shown in FIG. 9 which illustrates the tear 18 in the dura 17, the rootlets 21, the space containing cerebrospinal fluid 22, and bony side wall 23 of the spinal canal. With current technologies there would be a risk of damage due to a needle throw catching rootlets. With currently outlined embodiments, the rootlets would be protected, and in some cases no cerebrospinal drainage would be required. It is contemplated that during repairs described herein, cerebrospinal drainage, or a removal of a small quantity of cerebrospinal fluid could be performed, however other embodiments are envisioned without removal of the fluid; in either case less fluid removal would be required than versus methods of current technologies. Upon repair of the dura, methods described herein can also include additional repair steps such as glues or staples.

Figure 10:
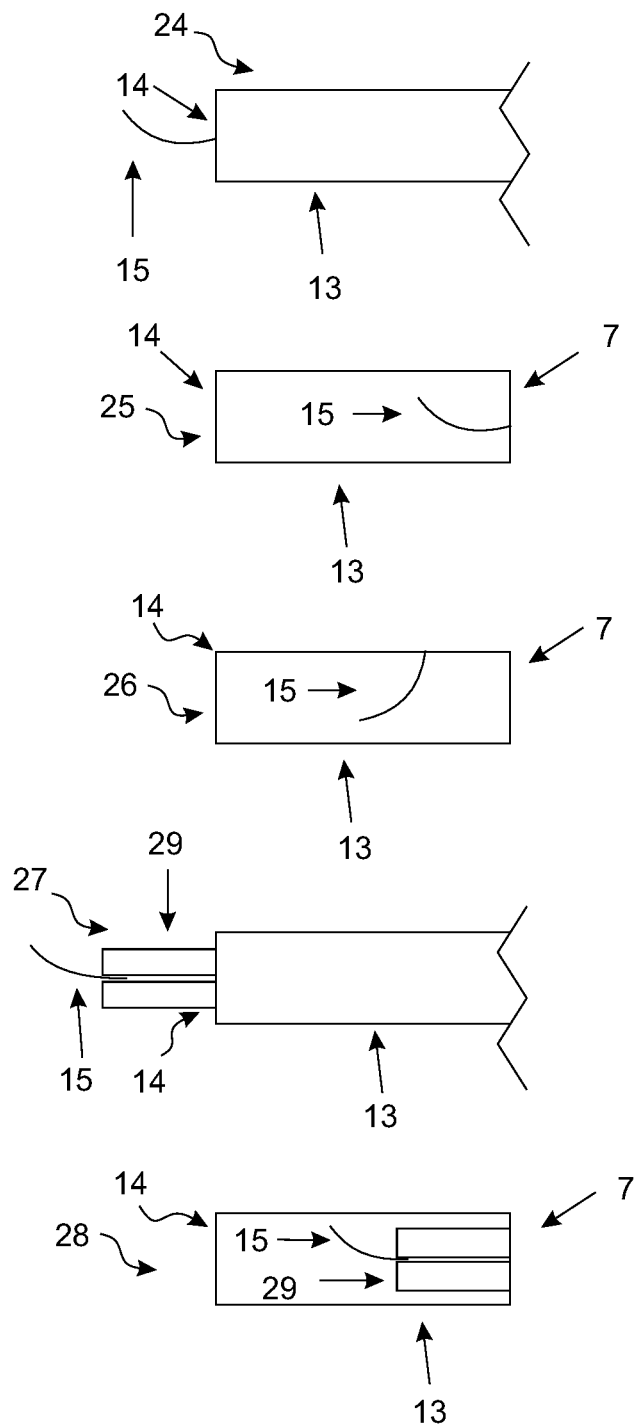
FIG. 10 illustrates the outer arm and mechanisms for holding the needle.

Example 4: Mechanisms for holding the needle. FIG. 1 outlined various mechanisms M for holding the needle. FIG. 10 illustrates various additional mechanism M embodiments. More specifically, FIG. 10 illustrates the outer arm 7 and example embodiments 24-28 of mechanisms M for holding the needle 15. The needle 15 can be held at or beyond the end opening 14 of the outer arm 7 as illustrated in embodiment 24, or can be held directly against or be otherwise attached to an inner wall of the outer arm 7 as shown in embodiments 25 and 26. The needle can slide into a hole or notch in the inner wall of the outer arm 7. The needles can be held by or an attachment or an extension coupled to the inner wall of the inner arm 7. The needle 15 can be held by jaws 29 as shown in embodiments 27 and 28. The jaws 29 can extend partially or fully out from the end opening 14 of the outer arm as in embodiment 27, or the jaws 29 and/or part or all of the needle 15 can be held partially or fully within the outer arm 7 as in embodiment 28. In specific embodiments the surfaces of the jaws 29 facing the needle 15 are smooth and a friction fit holds the needle 15. In other embodiments the jaws 29 have ridges or teeth for holding the needle 15. In other embodiments the needle 15 is placeable between the jaws 29 which are held together with spring force. In specific embodiments the jaws 29 can be set to various needle sizes, such as 1, 2, 3, 4 or 5 sizes, or from about 1 to about 10 sizes, and in specific embodiments the jaws 29 can be set to various position and locked in place to act as a clamp. In specific embodiments the force of the jaws 29 against the needle 15, when acting as a clamp, can be set for a tighter fit against the needle 15, as with a turning of a screw or electronic push of a button thereby moving the jaws 29 electronically; in other cases the settings are manually configured.

Figure 11:
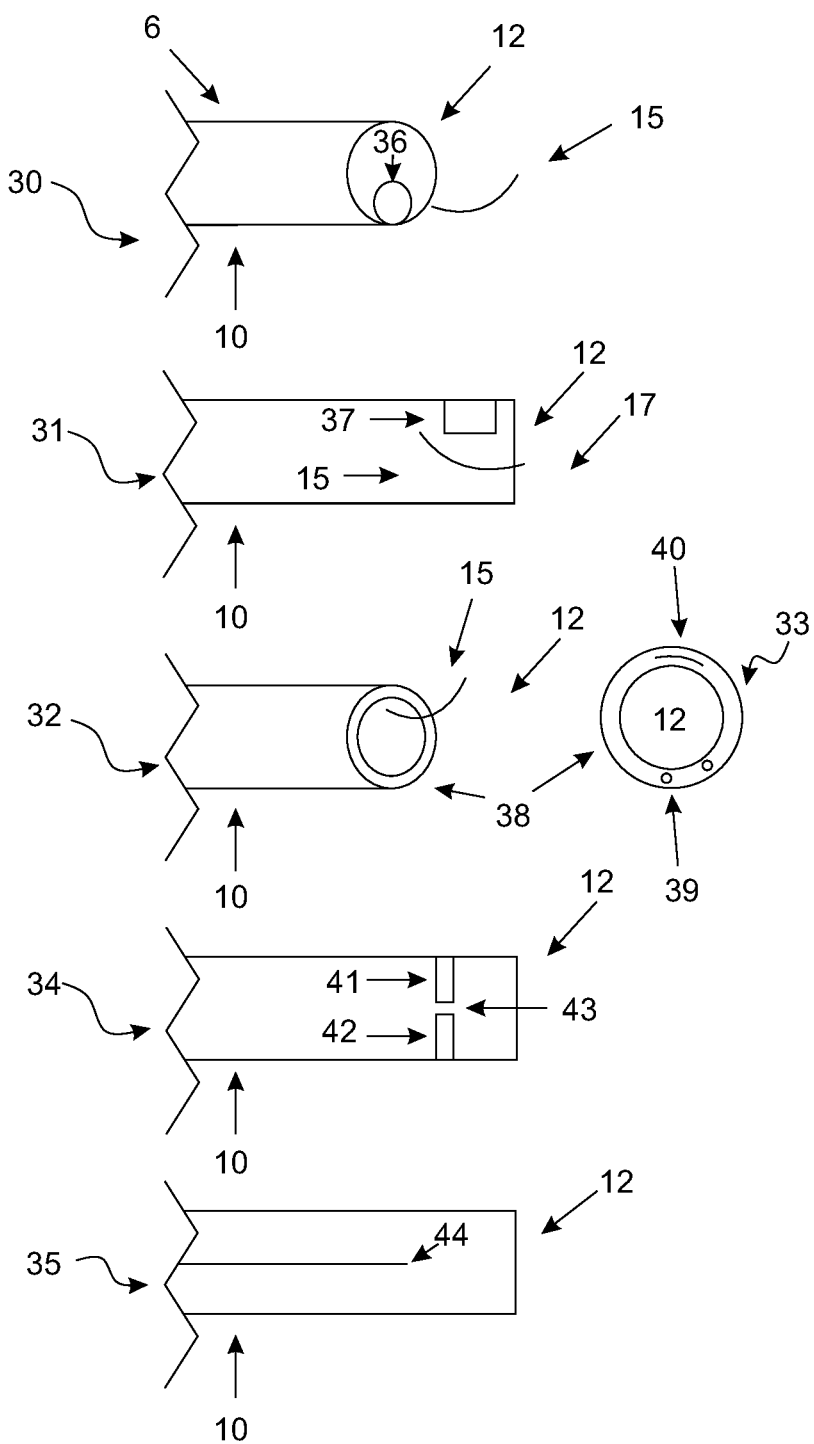
FIG. 11 illustrates the inner arm and mechanisms for catching the needle.

Example 5: Mechanisms for catching the needle. FIG. 11 illustrates the inner arm 6, platform 10, and end opening 12 and embodiments of mechanisms 30-35 for catching the needle 15. The needle 15 in specific embodiments is placeable through a loop 36, or partial loop where it is caught to allow needle 15 transfer as illustrated in embodiment 30 which shows the inner arm 6 at a slight angle such that the loop 36 can be clearly seen. Embodiment 31 is a longitudinal section of the inner arm 6. The needle 15 can be caught by a ledge 37 projecting out from an inner surface of the inner arm 6 as in embodiment 31. Specific embodiments include 1, 2, 3, 4, 5, or from about 1 to about 20, or from about 1 to about 10, or from about 3 to about 7, or from about 4 to about 6 ledges 37. In specific embodiments a ring 38 extends out from the inner surface of the inner arm 6, and the needle 15 is catchable at any point around the inner surface of the inner arm 6 via catching a portion of the ring 37 as shown in embodiment 32, which shows inner arm 6 at a slight angle. The needle 15 can slide over the ring 38 as the needle 15 is slid into the inner arm 6 as the inner arm 6 slides into the outer arm 7, and the needle 15 can be pulled back against a portion of the ring 38 as the inner arm 6 slides out of the outer arm 7 due to the fact the diameter of the inner arm 6 opening 12 at the point of the ring 38 is smaller than that of the outer arm end opening 14, and smaller than that as one moves into the inner arm 6 opening 12, beyond the ring 38. Embodiment 32 shows the inner arm 6 at a slight angle such that the ring 38 can be clearly seen. In specific embodiments the ring 38 is continuous. Specific embodiment 33 shows an end view of the inner arm 6 and the ring 38, including a hole 39, holes 39, and/or a slot 40 or slots 40 which can catch the needle 15. In specific embodiments the holes 39 and/or slots 40 into which the needle 15 can be placed are set at equal intervals from each other or at irregular intervals, and in specific embodiments there are, for example, from about 1, 2, 3, 4, 5, or from about 1 to about 20, or from about 1 to about 10, or from about 3 to about 7, or from about 4 to about 6 holes 39 and/or slots 40. The ring 38 can be placed directly at the inner arm 6 opening 12 or be set within or partially within the inner arm 6 opening 12. The ring 38 can be configured to be removable, reusable, or of single use. In specific embodiments various sizes of rings 38 can be used a single device 1. In specific embodiments the ring 38 is formed as part of the inner arm 6 of the device 1. Embodiment 34 shows a longitudinal section of the inner arm 6, where the needle 15 can form fit into extensions 41-42 of the inner 6 arm that form an opening 43 into which the needle 15 can fit by friction and/or engagement. Specific embodiments include from about 1, 2, 3, 4, 5, or from about 1 to about 20, or from about 1 to about 10, or from about 3 to about 7, or from about 4 to about 6 extensions. Embodiment 35 shows a longitudinal section of the inner arm 6, where the needle 15 can be transferred via a magnet 44 extending out from a portion of the inner arm 6. Any embodiment or embodiments as shown in 24-28 for holding the needle and/or embodiments 30-35 for catching the needle can use one or more magnets so that the needle is held, caught, and/or transferred. For example, extensions 41-42 can, in specific embodiments, be formed of or include 1 or more magnets each. Non-limiting examples of embodiments of magnets include permanent and/or electromagnets.

The invention claimed is:

1. A dural repair device operable with a single hand, the device comprising:
    a top section comprising a handle, wherein the handle comprises opposable arms squeezable by a single hand to move the opposable arms toward one another and toward a longitudinal midline of the device;
    a bottom section comprising an outer arm and an inner arm, wherein the outer arm and the inner arm are coupleable arms that oppose one another and are configured to move toward the longitudinal midline of the device upon squeezing of the handle, the outer arm comprising an end opening and a mechanism for holding a needle therewithin, and the inner arm comprising a heel, a platform, an end opening, and a mechanism for catching a needle from the outer arm, wherein the inner arm platform is slidable under an edge of dura so as to push rootlets away from the needle;
    wherein the device is configured such that the handle is activatable by squeezing to cause the inner and outer arms to couple and a needle from the outer arm to be caught by the mechanism for catching the needle within the inner arm, and is configured such that when the handle is released, the inner and outer arms are uncoupled, and the needle is transferred from the outer arm to the inner arm, allowing repair of the dura by suturing while protecting the needle from catching rootlets.

2. The device of claim 1, wherein the length of the platform is from about 2 mm to about 4 mm.

3. The device of claim 1, wherein prior to the handle activation, a maximum distance between the outer arm and inner arm end openings is less than about 1 cm.

4. The device of claim 1 wherein the handle opposable arms are squeezable by a single hand, wherein squeezing of the handle moves the outer arm and the inner arm toward the longitudinal midline of the device.

5. The device of claim 1 wherein the handle, the outer arm, and the inner arm are formed of a single piece.

6. The device of claim 1 wherein the handle comprises a shape-memory alloy.

7. The device of claim 1, further comprising a coupling between the handle and each of the outer and inner arms.

8. The device of claim 1, configured such that prior to the handle activation, a needle is held completely within the outer arm, and after the transfer of the needle to the inner arm, the needle is held completely within the inner arm, and no portion of the needle passes either of the arm openings until after the arms couple.

9. The device of claim 1, wherein the inner arm further comprises a tip extending out toward a longitudinal midline of the device farther than any portion of the platform or heel, and wherein the tip, platform, or heel have at least one curved portion that is slidable under an edge of dura configured to push rootlets away from the device.

10. The device of claim 1, wherein the heel and the platform comprise a continuous curve.

11. The device of claim 1, wherein the mechanism for catching a needle within the inner arm is a groove within a wall of the inner arm, a ring extending out from the inner arm, or a magnet.

12. The device of claim 1, wherein the mechanism for catching the needle within the inner arm is a groove within a wall of the inner arm.

13. The device of claim 12, wherein the inner arm further comprises a tip extending out toward a longitudinal midline of the device farther than any portion of the platform or heel, and wherein the tip, platform, or heel have at least one curved portion.

14. A method for dural repair, the method comprising:
    providing a device according to claim 1;
    positioning the outer arm and the inner arm of the device such that each of the arms straddles a side of a torn dura;
    pushing at least a portion of a nerve, rootlet, or spinal cord away from the device with a portion of the inner arm to prevent the nerve, rootlet, or spinal cord from being included in a suture line or knot;
    squeezing the handle of the device such that the inner and outer arms couple, and the needle is caught by the mechanism for catching a needle within the inner arm;
    releasing the handle such that the inner and outer arms uncouple, and the needle is transferred from the outer arm to the inner arm; and
    withdrawing the device from the dura, pulling suture coupled to the needle through the dura.

15. The method of claim 14, wherein the pushing is performed with at least a portion of the platform.

16. The method of claim 14, wherein the torn dura comprises a partially torn dura without cerebrospinal fluid leakage from the spinal canal, and wherein the step of pushing comprises moving the at least the portion of the nerve, rootlet, or spinal cord while it is floating in cerebrospinal fluid.

17. The method of claim 14, wherein cerebrospinal fluid is not drained during the repair procedure.

18. The method of claim 14, wherein the torn dura comprises a tear located at a bony side wall of the spinal canal.

19. The method of claim 14 wherein the torn dura has been damaged due to direct injury by instruments and/or during removal of attached tissues including scar tissue, a cyst, a disc or ligamentum flavum.

20. The device of claim 1 wherein the top section and the bottom section are formed of a single piece.

* * * * *